United States Patent [19]
Sibi et al.

[11] Patent Number: 6,080,857
[45] Date of Patent: Jun. 27, 2000

[54] METHOD OF PREPARATION OF β-AMINO ACIDS

[75] Inventors: Mukund Prahalada Rao Sibi; John Joseph Shay, both of Fargo, N. Dak.; Craig Peter Jasperse, Moorhead, Minn.; Mei Liu, Fargo, N. Dak.

[73] Assignee: North Dakota State University, Fargo, N. Dak.

[21] Appl. No.: 09/023,236

[22] Filed: Feb. 13, 1998

[51] Int. Cl.⁷ ...................... C07D 413/12; C07D 239/04; C07D 211/222; C07D 263/12; C07D 249/16
[52] U.S. Cl. ............................ 544/97; 544/316; 546/243; 546/221; 548/239; 548/220; 548/229; 548/257
[58] Field of Search .................................... 548/239, 220, 548/229, 257; 546/243, 221; 544/97, 316

[56] References Cited

U.S. PATENT DOCUMENTS 4,837,343  6/1989  Hatanaka et al. ........................ 549/291
5,681,820  10/1997  Ruminski .................................. 514/18

OTHER PUBLICATIONS

Amoroso, R. et al., "Lewis Acid–Promoted 1,4–Addition to Chiral Imide Derivatives in the Synthesis of β–Amino Acids," *J. Org. Chem.*, 58(21):5615–5619(1993).

Borman, S., "β–Peptides: Nature Improved?" *C&EN*, pp. 32–35 (Jun. 16, 1997).

Cole, D.C., *Tetrahedron*, 50:9517 (1994).

Corey, E.J., et al., "Highly Enantioselective and Diastereoselective Synthesis of β–Amino Acid Ester and β–Lactams from Achiral Esters and Imines," *Tetrahedron Letters*, 32:5287–5290 (1991).

Davies, I.W. et al., "The influence of ligand bite angle on the enantioselectivity of copper(II)–catalysed Diels–Alder reactions," *Chem. Commun.*, cover page, contents page and pp. 1753–1754 (1996).

Dumas, F. et al., "Investigating the π–Facial Discrimination Phenomenon in the Conjugate Addition of Amines to Chiral Crotonates: A Convenient Basis for the Rational Design of Chiral Auxiliaries," *J. Org.Chem.*, 61(7):2293–2299(1996).

Falborg, L. et al., "Asymmetric titanium–catalysed Michael addition of o–benzylhydroxylamine to α,β–unsaturated carbonyl compounds: synthesis of β–amino acid precursors," *J. Chem. Soc., Perkin Trans. 1*, pp. 2823–2826 (1996).

Ishihara, K. et al., "A New Chiral BLA Promoter for Asymmetric Aza Diels–Alder and Aldol–Type Reactions of Imines," *J. Am. Chem. Soc.*, 116(23):10520–10524 (1994).

Juaristi, E., et al., *J. Aldrichimica Acta*,27:3(1994).

Kashima, C. et al., "The Preparation of N–Acylpyrazoles and Their Behavior Toward Alcohols," *Synthesis*, pp. 61–65 (Jan. 1994).

Koert, U., "β–Peptides: Novel Secondary Structures Take Shape," *Angew. Chem. Int. Ed. Engl.*, 36(17):1836–1837(1997).

Rico, Joseph G. et al., "A Highly Stereoselective Michael Addition to an α,β–Unsaturated Ester as the Crucial Step in the Synthesis of a Novel β–Amino Acid–Containing Fibrinogen Receptor Antagonist," *J. Org. Chem.*, 58(27):7948–7950 (1993).

Seebach, D. et al., "β–Peptides: a surprise at every turn," *Chem. Commun.*, pp. 2015–2022 (1997).

Sibi, M.P. et al., "Chiral Lewis Acid catalysis in Radical Reactions: Enantioselective Conjugate Radical Additions," *J. Am. Chem. Soc.*, 118(38):9200–9201 (1996).

Sibi, M.P. et al., "Enantioselective Intermolecular Free Radical Conjugate Additions. Application of a Pyrazole Template," *Tetrahedron Letters*, 38:5955–5958(1997).

Sibi, M.P. et al., "Practical and Efficient Enantioselective Conjugate Radical Additions," *J. Org. Chem.*,62(12): 3800–3801 (1997).

Bratschi et al., Syntheis and Stereochemical Behavior of . . . , Tetrahedron (50)9 2996–2964, Dec. 1994.

*Primary Examiner*—Joseph K. McKane
*Assistant Examiner*—Dominic Keating
*Attorney, Agent, or Firm*—Merchant & Gould P.C.

[57] ABSTRACT

A method for the preparation of β-amino acid compounds is provided. The method includes contacting an amine nucleophile with an α,β-unsaturated amide compound in the presence of a chiral Lewis acid complex. The chiral Lewis acid complex is formed from an azophilic metal salt and a chiral bisoxazolinylmethane compound. The selective amidolysis of one enantiomer of the β-aminoamide product is also described.

21 Claims, No Drawings

METHOD OF PREPARATION OF β-AMINO ACIDS

BACKGROUND OF THE INVENTION

There has been an increasing interest in optically active β-amino acids and peptides derived from them. Optically active β-amino acids include a number of naturally occurring substances in the free form with an interesting pharmacological profile. Functionalized β-amino acids are important segments of bioactive molecules. For example, Taxol™ contains the phenylisoserine side chain as its key pharmacophore, and compounds of cyclic β-amino acids make up the class of β-lactam antibiotics. Additionally, β-amino acids are components of peptidic natural products with a wide range of biological activity. Peptides consisting of β-amino acids have promising pharmaceutical use as orally active drugs since they are hydrolytically stable. Given the significance of the β-amino acids, development of new methodologies for their synthesis, especially for the stereoselective synthesis of chiral β-amino acids, is important.

Among the strategies for the synthesis of racemic β-amino acids is the conjugate addition of nitrogen nucleophiles to enoates. Other common approaches include diastereoselective additions in which the nitrogen nucleophile or the α,β-unsaturated substrate is chiral. Typical examples include the Michael type addition of optically active lithium amides to α,β-unsaturated esters, or additions of amines to chiral α,β-unsaturated esters. These approaches however, require the use of stoichiometric amounts of expensive optically active reagents which limits their utility. A single example of chiral Lewis acid catalysis in the conjugate addition of amines to enoates has been reported, however, this method proceeds with only low to moderate selectivity (highest ee of 42%).

The current methods for the synthesis of chiral β-amino acids suffer from one or more of a number of disadvantages such as low yields, use of costly reagents, intricate purification steps or low enantiomeric excesses. Accordingly, in view of the potential pharmaceutical utility of β-amino acids and β-peptides there is a continuing need for methods which would permit the efficient, large scale preparation of β-amino acids, especially in optically active form.

SUMMARY OF THE INVENTION

The present invention provides a method for the preparation of β-amino acid compounds through the conjugate addition of an amine nucleophile to an α,β-unsaturated amide compound in the presence of a chiral Lewis acid complex. The chiral Lewis acid complex can be prepared from an azophilic metal salt and a chiral bisoxazolinylmethane ligand. The method provides a high yielding syntheses of β-amino acids and related derivatives from readily available starting materials and is amenable to large scale synthesis. Moreover, the present method yields these β-amino acid compounds in high enantiomeric excesses.

The method includes contacting the α,β-unsaturated amide compound with an amine nucleophile in the presence of the chiral Lewis acid complex to form a chiral β-aminoamide. The method is typically carried out at room temperature or below in an organic solvent using catalytic or stoichiometric amounts of the chiral Lewis acid with respect to the α,β-unsaturated amide compound.

The high enantiomeric excesses of the present method are believed in part to be related to a selective amidolysis of the minor enantiomer produced. The unique catalytic nature of the present method is based at least in part on the fact that the α,β-unsaturated amide compound substrate is a better Lewis base than the β-amino acid compound product. Once a majority of the of the α,β-unsaturated amide compound substrate is consumed, the minor enantiomer of the initially formed chiral β-aminoamide undergoes a faster rate of amidolysis with residual amine nucleophile to form a second β-aminoamide, thereby increasing the enantiomeric excess of the initially formed chiral β-aminoamide product.

DETAILED DESCRIPTION OF THE INVENTION

The present invention provides a method for the preparation of β-amino acids from α,β-unsaturated amide compounds. The method involves contacting the α,β-unsaturated amide compound with an amine nucleophile in the presence of an organic solvent and a chiral Lewis acid complex. The method is typically carried out at about room temperature (roughly 25° C.) or below. Temperatures of about −20° C. to about −80° C. are preferably employed in order to maintain a convenient reaction rate without substantially decreasing the yield or enantioselectivity. The reaction is typically carried out in an organic solvent which does not coordinate too strongly to the Lewis acid complex, e.g. a chlorinated organic solvent. Examples of suitable chlorinated organic solvents are methylene chloride, chloroform, or dichloroethane. Examples of other suitable organic solvents include ethers, such as methyl tert-butyl ether, aromatics, such as toluene, or acetonitrile. Preferably the organic solvent has a freezing point no more than about −100° C.

The reaction time necessary to carry out the present invention will vary depending on temperature, amine nucleophile, and chiral Lewis acid complex utilized. Typical reaction times range from 1.5 to 72 hours. Shorter or longer reaction times may be achieved by altering the reaction conditions.

In order to initiate amidolysis of the minor enantiomer thereby increasing the enantiomeric excess of the desired product, the present method typically employs a molar ratio of the amine nucleophile to the α,β-unsaturated amide compound of about 0.5:1 to about 1.2:1. Preferably, a slight molar excess of the amine nucleophile is employed, e.g., a molar ratio to the α,β-unsaturated amide compound of about 1.0:1 to about 1.2:1.

The present method is typically carried out with the chiral Lewis acid complex in a ratio of about 0.1:1 to about 1:1 with the α,β-unsaturated amide compound. Preferably, the chiral Lewis acid complex is in a molar ratio with the α,β-unsaturated amide compound of about 0.25:1 to about 0.40:1. The chiral Lewis acid complex typically if formed from a mixture of bisoxazolinylmethane ligand and azophilic metal salt in a molar ratio of at least about 1:1. Preferably the molar ratio of ligand to metal salt used to form the chiral Lewis acid complex is about 1:1 to about 1.1:1.

The Lewis acid complex employed in the present method typically is formed from a chiral bisoxazolinylmethane compound and a salt of an azophilic metal cation. As used herein such "azophilic metal cations" refer to those metal cations capable of coordination with nitrogen atoms of a ligand. The azophilic metal cation is preferably not too strongly azophilic to avoid selectively coordinating with the amine nucleophile in preference to the bisoxazolinylmethane compound. Examples of suitable azophilic metal cations include $Zn^{2+}$, $Mg^{2+}$, $Sn^{2+}$, $Sc^{3+}$, $Y^{3+}$, and lanthanide cations. Preferably, the azophilic metal cation is $Mg^{2+}$, $Zn^{2+}$, $Yb^{3+}$, $Y^{3+}$, or $Eu^{3+}$, with magnesium salts being particularly suitable. Included among suitable counterions are chlorine anion, bromine anion, iodine anion, and triflate anion. For economic and efficacy reasons, chloride and/or bromide counteranions are preferably used. Examples of particularly suitable azophilic metal salts include $MgCl_2$ and $MgBr_2$. Another group of particularly suitable azophilic metal salts include the triflate salts of $Mg^{2+}$, $Zn^{2+}$, $Yb^{3+}$, $Y^{3+}$, and $Eu^{3+}$.

The chiral Lewis acid complex employed in the present method is typically formed from a salt of an azophilic metal cation and a bisoxazolinylmethane compound. Examples of suitable bisoxazolinylmethane compounds include those substituted at any combination of the 4, 4', 5, and 5' positions to afford a chiral molecule. The substitution is typically such that symmetry of the molecule is maintained so as to avoid problems associated with more than one isomer of the resulting metal complex. Typical substituents include bulky alkyl, cycloalkyl, aryl, or arylalkyl groups and are preferably located at the 4 and 4' positions. Other typical substituents include cycloalkyl, aryl or arylalkyl systems which individually bridge the 4, 5 and 4', 5' positions. Suitable bisxazolinylmethane ligands are represented by the formula:

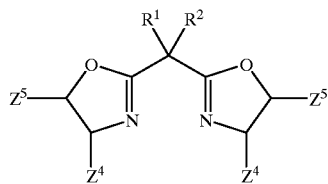

Typically, $R^1$ and $R^2$ are independently hydrogen, alkyl, arylalkyl, or $R^1$ and $R^2$ together are $-(CH_2)_n-$, where n=2–6. Preferably, $R^1$ and $R^2$ are identical and chosen from the group of hydrogen, lower alkyl (e.g., methyl), or benzyl. In another preferred embodiment of the present method, $R^1$ and $R^2$ together form a spiro alkyl ring group, such as a cyclopropyl group, which optionally may be substituted with one or more alkyl groups. The $Z^4$, $Z^{4'}$, $Z^5$, and $Z^{5'}$ groups are typically alkyl, cycloalkyl, aryl, or arylalkyl groups. Preferably, $Z^4$, $Z^{4'}$, $Z^5$, and $Z^{5'}$ are iso-propyl, tert-butyl, benzyl, phenyl, or diphenylmethyl. In one particularly suitable embodiment of the invention, $Z^4$, $Z^{4'}$, $Z^5$, and $Z^{5'}$ form an indan groups with the oxazoline rings affording a ligand represented by the formula:

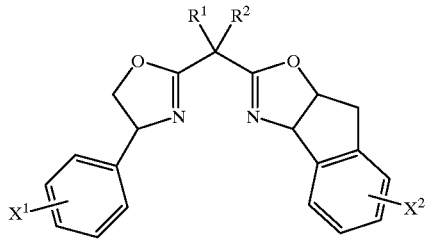

where $R^1$ and $R^2$ are independently hydrogen, alkyl, arylalkyl, or $R^1$ and $R^2$ together are $-(CH_2)_n-$, where n=2–6. Preferably, $R^1$ and $R^2$ are identical and are selected from hydrogen, lower alkyl (i.e. $C_1$–$C_6$ alkyl), or benzyl. Most preferably, $R^1$ and $R^2$ together form a cyclopropyl group. $X^1$ and $X^2$ are preferably identical and are selected from hydrogen, alkyl, alkoxy, halo, haloalkyl, cyano, nitro, or $CO_2R'$, wherein $R'$ is alkyl, cycloalkyl, or arylalkyl.

The amine nucleophiles employed in the present invention are typically sterically bulky and preferably include substituents which are easily removed in a subsequent reaction to produce the free amine or amine salt. Amine nucleophiles typically employed in the present method are O-substituted amines or amines with bulky alkyl, cycloalkyl, aryl or arylalkyl substituents. The amine nucleophiles preferably are substituted with alkyl, cycloalkyl, aryl or arylalkyl groups having no more than about 20 carbon atoms. Examples of suitable amine nucleophiles include arylmethylamines, N-arylmethylhydroxylamines, O-arylmethylhydroxylamines, diarylmethylamines, or O-diarylmethylhydroxylamines, or N-diarylmethylhydroxylamines. Preferred amine nucleophiles include benzylamine, N-benzylhydroxylamine, aminodiphenylmethane. One particularly suitable amine nucleophile is O-benzylhydroxylamine. Other examples of possible amine nucleophiles include secondary amines, such as morpholine, and aromatic amines having a protonated nitrogen atom (in an uncharged form), such as 3,5-dimethylpyrazole.

The present method employs α,β-unsaturated amide compounds capable of coordinating with the chiral Lewis acid complex. The α,β-unsaturated amide compound is generally selected to faciliate subsequent conversion of the product to a free carboxylic acid or carboxylic acid salt. The α,β-unsaturated amide compound is typically an α,β-unsaturated carboxylic acid which has been protected with an amide producing acid derivatizing group. The result of such protection produces a species capable of coordinating to the Lewis acid complex. Typically, the amide producing acid derivatizing group provides a second coordination site capable of coordinating to the metal cation in addition to the acyl oxygen of the amide group. Included among suitable amide producing acid derivatizing group are:

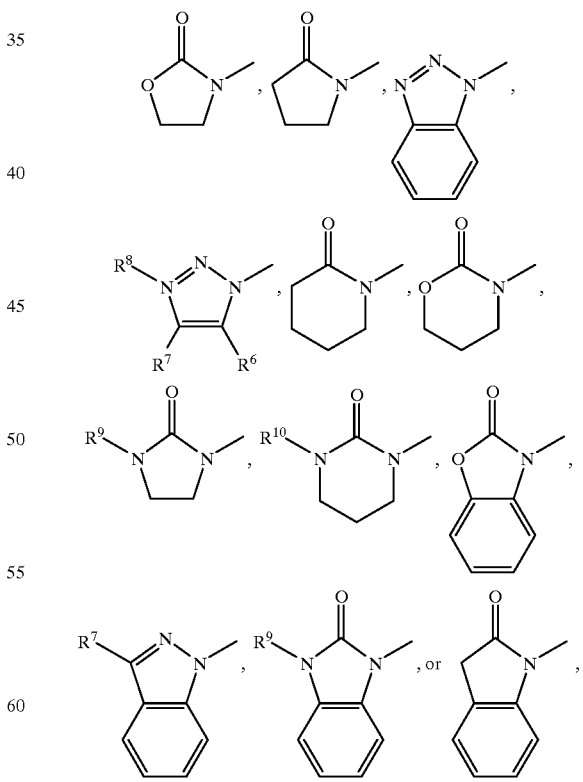

where $R^6$ and $R^8$ are typically identical and chosen from the group hydrogen or $C_1$–$C_6$ alkyl. $R^7$ is typically hydrogen, alkyl, arylalkyl, or aryl, and $R^9$ and $R^{10}$ are generally independently chosen from hydrogen, alkyl, cycloalkyl, aryl, or arylalkyl. Examples of preferred α,β-unsaturated amide compounds include isoxazolidinone, 2-pyrrolidinone, and benzotriazole protected crotonates. A particularly suitable α,β-unsaturated amide compound is 3,5-dimethyl pyrazole protected crotonate. The α,β-unsaturated amide compound may optionally be an α,β-unsaturated amide substituted or disubstituted at the β-position by an aryl, alkyl, or cycloalkyl substituent. For example, the α,β-unsaturated amide may be a compound having the formula:

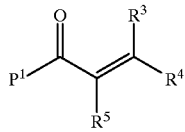

wherein P¹ is an amide producing acid derivatizing group such as those described above, and R³, R⁴ and R⁵ are independently hydrogen, alkyl, cycloalkyl, aryl, or arylalkyl. At least one of R³ and R⁴ is not hydrogen, and R³ and R⁴ are not the same. Typical substituents at the β-position include lower alkyl, cycloalkyl, phenyl and phenylalkyl, optionally substituted with one or more common organic substituent groups. Preferably, R³ and R⁵ are hydrogen and R⁴ is an group having up to about 20 carbon atoms selected from alkyl, cycloalkyl, phenyl and phenylalkyl (e.g., benzyl or phenethyl).

The present method is generally characterized by high enantiomeric excesses which may be enhanced by selective amidolysis of one enantiomer of the product of the nucleophilic addition, in the presence of a chiral Lewis acid complex. Typically, reaction times are extended so as to allow selective amidolysis of the initial product of the nucleophilic addition to produce a second β-aminoamide. Included as typical products of selective amidolysis are those with the formula:

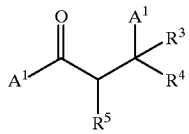

where R³, R⁴, and R⁵ are individually selected from the group hydrogen, alkyl, cycloalkyl, aryl, or arylalkyl, and at least one of R³ and R⁴ is not hydrogen, A¹ is —NHR¹⁶, —N(OH)R¹⁶, —N(OR¹⁶)H, and R¹⁶ is an alkyl, arylalkyl, or cycloalkyl group. In a typical embodiment of the method, the resulting product from the conjugate addition of O-benzylhydroxylamine to 3,5-dimethyl pyrazole protected crotonate, in the presence of a chiral Lewis acid complex proceeds through re face amine addition to an s-cis-substrate/Lewis acid/ligand complex with a tetrahedral or a cis octahedral arrangement. The catalytic nature of the addition shows that the substrate is a better Lewis base than the product. Once a majority of the starting material is consumed (~80%), the minor enantiomer undergoes faster amidolysis thereby increasing the enantiomeric excess of the desired product, as well as to reduce its chemical yield somewhat. This combination of efficient conjugate addition followed by selective destruction of the minor enantiomer disclosed in the present method provides for high enantiomeric excesses of the highly desirable β-aminoamide compounds.

The present invention also includes the selective amidolysis, in the presence of the chiral Lewis acid complex, of a β-aminoamide to produce a second β-aminoamide. Suitable β-aminoamides which can be employed in this method are of the formula:

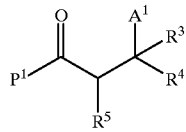

where A₁ is typically —NHR¹⁶, —N(OH)R¹⁶, or —N(OR¹⁶)H, and R¹⁶ is an alkyl, arylalkyl, or cycloalkyl group. R³, R⁴ and R⁵ are independently hydrogen, alkyl, cycloalkyl, aryl, or arylalkyl, and at least one of R³ and R⁴ is not hydrogen, and R³ and R⁴ are not the same. P¹ is selected from the group

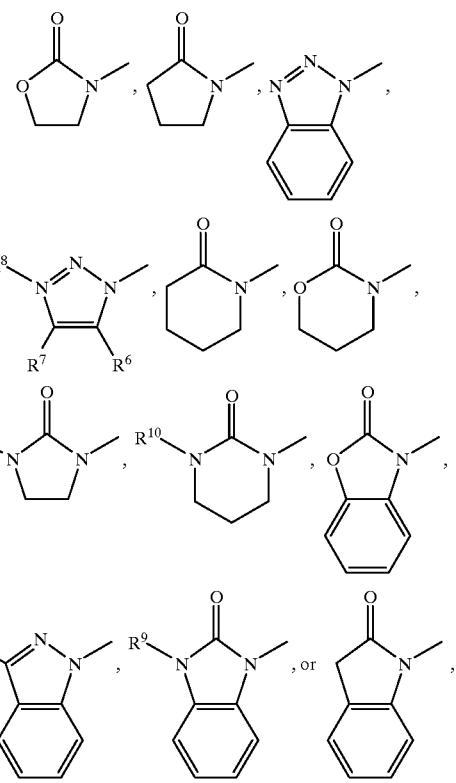

where R⁶ and R⁸ are identical and selected from hydrogen or C₁–C₆ alkyl, R⁷ is hydrogen, alkyl, arylalkyl, or aryl, and R⁹ and R¹⁰ are independently hydrogen, alkyl, cycloalkyl, aryl, or arylalkyl. This selective amidolysis of an initial β-aminoamide produces a second β-aminoamide having the formula:

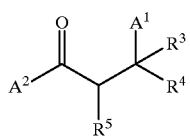

where $A^2$ is typically —$NHR^{17}$, —$N(OH)R^{17}$, or —$N(OR^{17})H$, and $R^{17}$ is an alkyl, arylalkyl, or cycloalkyl group.

The present method may also include cleaving the initially formed chiral β-aminoamide to form a chiral β-$NH_2$-carboxamide. This can be accomplished, for example, by reductive cleavage of the substituent of the β-amino group to afford the free amine or salt thereof at the β-position. If desired, this cleavage reaction may be carried out after hydrolysis of the initially formed β-aminoamide to the corresponding β-aminocarboxylic acid. Suitable β-aminoamides and β-aminocarboxylic acids include those whose amino groups have substituents which are readily cleaved under reductive conditions. For example, the substituent of β-aminoamides and β-aminocarboxylic acids with a β-amino group, such as an arylmethylamine, N-arylmethylhydroxylamine, O-arylmethyl-hydroxylamine, diarylmethylamine, O-diarylmethylhydroxylamine, or N-diarylmethyl-hydroxylamine, are readily cleaved under reductive conditions. Typical methods for such reductive cleavage involve the use of a source of hydrogen (e.g., gaseous hydrogen ($H_2$) or in situ hydrogen sources such as cyclohexene, ammonium formate and the like) and a metal catalyst such as palladium or platinum. Suitable methods for such conversions are described in *Protective Groups in Organic Synthesis,* Greene, ed., John Wiley & Sons, New York (1981) and *Protecting Groups,* Koeienski, Thieme, Stuttgart (1994), the disclosure of which are incorporated herein by reference.

In addition, the product(s) of the present method may be hydrolyzed to form a chiral β-aminocarboxylic acid or salt thereof. The hydrolysis reaction may be carried out directly on the initially formed chiral β-aminoamide to form a chiral β-aminocarboxylic acid or salt thereof. Alternatively, the initially formed chiral β-aminoamide may be converted into a chiral β-$NH_2$-carboxamide by removal of the substituents from the β-amino group prior to hydrolysis. The hydrolysis reaction may be conveniently carried out by exposing the chiral carboxamide to acidic or basic aqueous conditions.

EXAMPLES

The invention will be further exemplified by the following examples. These examples serve to illustrate but are not meant to limit the scope of the invention.

Example I
Stoichiometric Chiral Lewis Acid Catalyzed Amine Additions

Under $N_2$, to a flask containing $MgBr_2.Et_2O$ (0.1 mmol) and bisoxazoline 2 (0.1 mmol) was added $CH_2Cl_2$ (3 mL). Pyrazole crotonate 1 (0.1 mmol) (in 1 mL $CH_2Cl_2$) was added and the mixture was allowed to stir for 30 min. The reaction was cooled to −60° C. and $H_2NOCH_2Ph$ (0.11 mmol) (in 1.1 mL $CH_2Cl_2$) was added. The reaction was monitored by TLC and when judged complete was quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by HPLC. The results are presented in Table I below (entries 1a–1f). Yields shown are isolated yields of adducts 3a and 3b, where 3a is the major adduct produced.

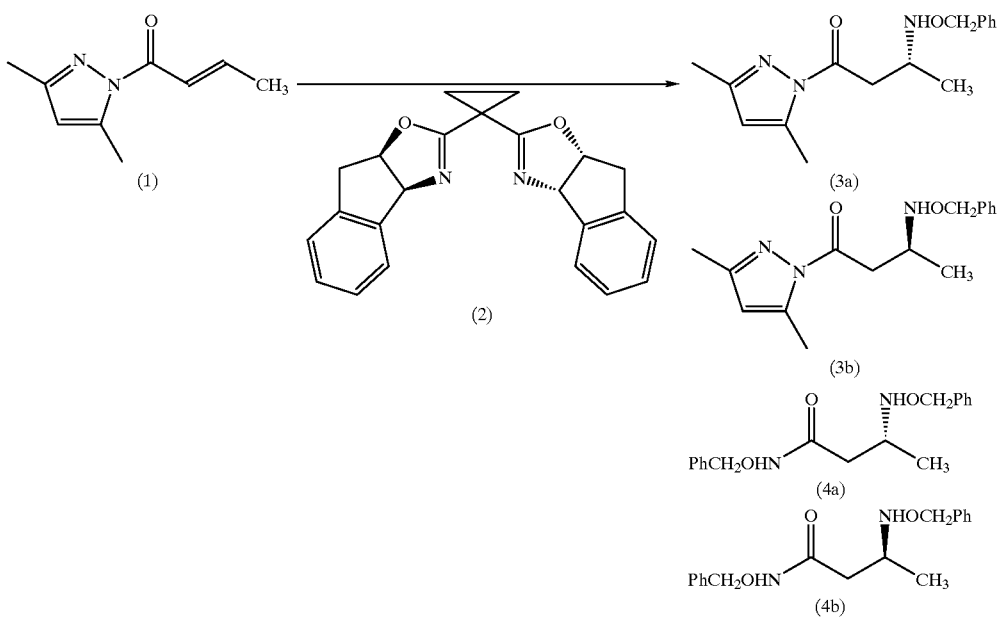

Example II
Substoichiometric Chiral Lewis Acid Catalyzed Amine Additions

Under $N_2$, to a flask containing equimolar amounts of $MgBr_2.Et_2O$ and bisoxazoline 2 was added 20 mL of $CH_2Cl_2$. The amounts of Lewis acid ("LA") and ligand employed in individual experiments are shown in Table I. Pyrazole crotonate 1 (0.5 mmol) was added as a solution in 5 mL $CH_2Cl_2$ and stirred for 30 min. The reaction was cooled to −60° C. and $H_2NOCH_2Ph$ (0.55 mmol) was added as a solution in 5.5 mL $CH_2Cl_2$. The reaction was monitored by TLC and when judged complete was quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by HPLC. The results of the experiments are shown in Table I below (entries 2a–2d).

The amounts of Lewis acid and ligand employed, as expressed in Table I, are based on the amount of pyrazole crotonate employed. Yields shown are isolated yields of adducts 3a and 3b, where 3a is the major adduct produced.

TABLE I

Effect of Temperature and Catalyst

| Entry | Eqs. LA | Temp. (° C.) | Time (hr) | Yield, %[a] | ee, % |
|---|---|---|---|---|---|
| 1a | 1.0 | −80 | 1.5 | 39 | 79 |
| 1b | 1.0 | −80 | 17 | 53 | 80 |
| 1c | 1.0 | −80 | 48 | 57 | 91 |
| 1d | 1.0 | −80 | 72 | 60 | 97 |
| 1e | 1.0 | −60 | 21 | 62 | 96 |
| 1f | 1.0 | 0 | 2 | 41 | 80 |
| 2a | 0.3 | −60 | 20 | 63 | 93 |
| 2b | 0.2 | −60 | 17 | 77 | 84 |
| 2c | 0.1 | −60 | 48 | 87 | 79 |
| 2d | 0.05 | −60 | 48 | 59[b] | 49 |

[a]Isolated yields after chromatography.

Example III

Kinetic Resolution of Racemic β-Amino Acid Compounds

Under $N_2$, to a flask containing $MgBr_2.Et_2O$ (0.1 mmol) and bisoxazoline 2 (0.1 mmol) was added $CH_2Cl_2$ (4 mL). Racemic pyrazole 3 (0.1 mmol) in 0.9 mL $CH_2Cl_2$ was added and the mixture was allowed to stir for 30 min. The reaction was cooled to −60° C. and the appropriate amount of 0.1 M $H_2NOCH_2Ph$ in $CH_2Cl_2$ was added. After 3 h the reaction was quenched with $H_2O$ and extracted with $CH_2Cl_2$. The combined organics were dried ($MgSO_4$) and concentrated. The products were purified by preparative TLC (50% ethylacetate/hexanes). The results of a number of experiments following this procedure using various equivalents of Lewis acid (LA) catalyst and amine nucleophile are reported in Table II below. As before the enantiomeric excess (% ee) of each product was determined by chiral HPLC analysis.

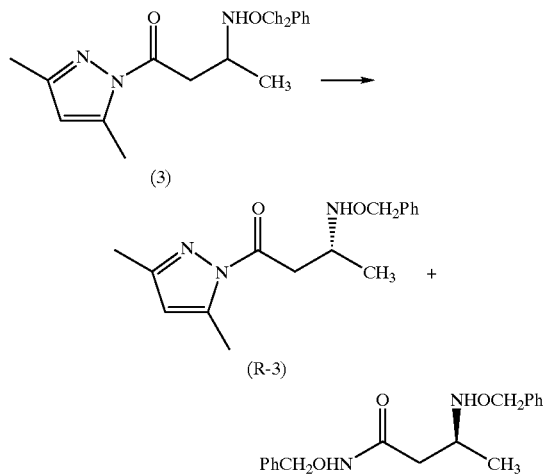

TABLE II

Enantioselective Amidolysis of Racemic β-Amino Acids Compounds[a]

| Entry | Chiral LA Eqs | Amine Eqs | Time, hr | Temp. ° C. | % 3 (% ee) | % 4 (% ee) |
|---|---|---|---|---|---|---|
| 3a | 1.0 | 1.0 | 3 | −60 | 36 (52) (R) | 46 (30) (S) |
| 3b | 1.0 | 0.5 | 3 | −60 | 47 (47) (R) | 34 (60) (S) |
| 3c | 0.3 | 0.5 | 24 | −60 | 71 (60) (R) | 24 (36) (S) |
| 3d | 0.3 | 0.3 | 24 | −60 | 74 (3) (R) | 18 (47) (S) |

[a]Isolated after chromatography.

Example IV

Chiral Lewis Acid Catalyzed Amine Additions to Various to α-β Unsaturated Amides Under $N_2$, to a flask containing $MgBr_2.Et_2O$ (0.1 mmol) and bisoxazoline 2 (0.1 mmol) was added $CH_2Cl_2$ (3 mL). α,β-Unsaturated amide (0.1 mmol) (in 1 mL $CH_2Cl_2$) was added and the mixture was allowed to stir for 30 min. The reaction was cooled to −60° C. and $H_2NOCH_2Ph$ (0.11 mmol) in 1.1 mL $CH_2Cl_2$ was added. The reaction was monitored by TLC and when judged complete was quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by chiral HPLC analysis. The results of a number of experiments following this procedure using various α,β-unsaturated amides are reported in Table III below.

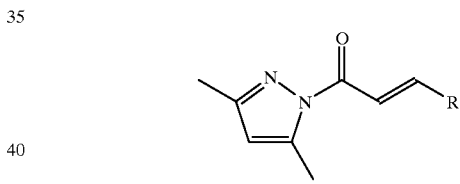

TABLE III

Conjugate Addition of $H_2NOCH_2Ph$ to α-β Unsaturated amides

| Entry | R | Time, h | Yield, %[a] | ee, % |
|---|---|---|---|---|
| 4a | —$CH_2CH_3$ | 21 | 56 | 92 |
| 4b | —$CH_2C_6H_{11}$[c] | 22 | 39 | 90 |
| 4c | —$CH_2Ph$ | 22 | 46 | 97 |
| 4d | -i-Pr | 21 | 41 | 83 |
| 4e | -Ph | 72 | 21[b] | 78 |

[a]Yields are for isolated and column purified materials.
[b]70% of the starting material was recovered.
[c]cyclohexylmethyl

Example V

Effect of Ligand on Conjugate Addition

Under $N_2$, to a flask containing $MgBr_2.Et_2O$ (0.1 mmol) and one of a variety of chiral bisoxazolinylmethane ligands (0.1 mmol) was added $CH_2Cl_2$ (3 mL). The various chiral bisoxazolinylmethane ligands were prepared according to the general procedure disclosed in Davies et al., *J. Chem.*

Soc. Chem. Commun. 1753 (1996), the disclosure of which is incorporated by reference. Pyrazole crotonate 1 (0.1 mmol) in 1 mL $CH_2Cl_2$ was then added and the mixture was allowed to stir for 30 min. The reaction was cooled to −60° C. then $H_2NOCH_2Ph$ (0.11 mmol) in 1.1 mL $CH_2Cl_2$ was added. The reaction mixture was stirred for 21 hours at −60° C. and then quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity of the β-aminoamide product was determined by chiral HPLC. The results of a number of experiments following this procedure using various ligands are reported in Table IV below.

TABLE IV

| Effect of Ligand on Conjugate Addition | | |
|---|---|---|
| Ligand | Yield, %[a] | ee, % |
| 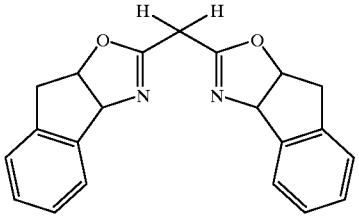 | 29 | 54 (R) |
| 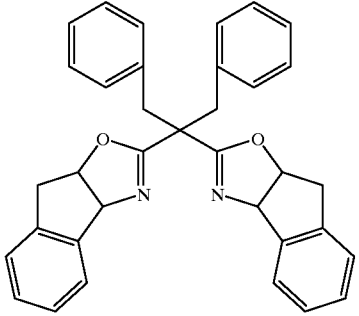 | −63 | 65 (R) |
| 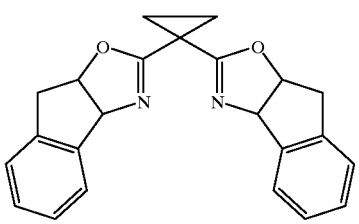 | 62 | 96 (R) |
| 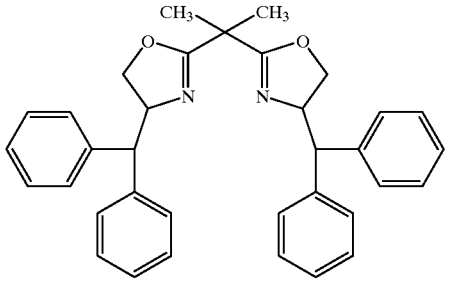 | 20 | 39 (R) |

TABLE IV-continued

Effect of Ligand on Conjugate Addition

| Ligand | Yield, %[a] | ee, % |
|---|---|---|
| (bisoxazoline with H,H bridge and phenyl substituents at 4,5 positions) | 4 | 3 (R) |

[a]Yields are for isolated and column purified materials.

Example VI
Effect of Lewis Acid on Enantioselectivity

Under $N_2$, to a flask containing one of a variety of azophilic metal salts (0.1 mmol) and bisoxazoline 2 (0.1 mmol) was added $CH_2Cl_2$ (3 mL). Pyrazole crotonate 1 (0.1 mmol) in 1 mL $CH_2Cl_2$ was added and the mixture was allowed to stir for 30 min. The reaction was cooled to −60° C. and $H_2NOCH_2Ph$ (0.11 mmol) in 1.1 mL $CH_2Cl_2$ was added. The reaction continued for a varying amount of time (as indicated in Table V) and was quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by chiral HPLC. The results of a number of experiments following this procedure using various ligands are reported in Table V below.

TABLE V

Effect of Lewis Acid on Enantioselectivity

| Entry | Lewis Acid | Time, h | % Yield | % ee (stereochemistry) |
|---|---|---|---|---|
| 1 | Mg(OTf)$_2$ | 48 | 35 | 41 (R) |
| 2 | MgI$_2$ | 22 | 61 | 13 (S) |
| 3 | MgBr$_2$ | 21 | 62 | 96 (R) |
| 4 | ZnBr$_2$ | 48 | 24 | 8 (R) |
| 5 | Zn(OTf)$_2$ | 48 | 10 | 40 (R) |
| 6 | ZnI$_2$ | 48 | 0 | — |
| 7 | Yb(OTf)$_3$ | 22 | 76 | 41 (S) |
| 8 | Y(OTf)$_3$ | 22 | 65 | 43 (S) |
| 9 | Sn(OTf)$_2$ | 22 | 15 | 9 (S) |
| 10 | Sc(OTf)$_3$ | 22 | 48 | 10 (S) |
| 11 | La(OTf)$_3$ | 22 | 24 | 0 |
| 12 | Eu(OTf)$_3$ | 22 | 60 | 45 (S) |

Example VII
Effect of Solvent on Enantioselectivity

Under $N_2$, to a flask containing $MgBr_2 \cdot Et_2O$ (0.1 mmol) and bisoxazoline 2 (0.1 mmol) was added various solvents (3 mL). Pyrazole crotonate 1 (0.1 mmol) (in 1 mL $CH_2Cl_2$) was added and the mixture was allowed to stir for 30 min. The reaction mixture was cooled to −60° C., except for the acetonitrile entry which was run at 25° C., and $H_2NOCH_2Ph$ (0.11 mmol) in 1.1 mL $CH_2Cl_2$ was added. The reaction continued for 22 hours at the indicated temperature and then was quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by chiral HPLC. The results of a number of experiments in differing solvents following this procedure are reported in Table VI below.

TABLE VI

Effect of Solvent on Enantioselectivity

| Entry | Solvent | Temp, ° C. | Time, h | %, Yield | %, ee (stereochemistry) |
|---|---|---|---|---|---|
| 1 | Toluene | −60 | 22 | 46 | 80 (R) |
| 2 | CH$_2$Cl$_2$ | −60 | 22 | 62 | 96 (R) |
| 3 | Acetonitrile | 25 | 22 | 31 | 31 (R) |

Example VIII
Effect of α,β-Unsaturated Amide Substrate on Conjugate Addition Under $N_2$, to a flask containing $MgBr_2 \cdot Et_2O$ (0.1 mmol) and bisoxazoline 2 (0.1 mmol) was added $CH_2Cl_2$ (3 mL). α,β-Unsaturated amide (0.1 mmol) (in 1 mL $CH_2Cl_2$) was added and the mixture was allowed to stir for 30 min. The reaction was cooled to −60° C. then $H_2NOCH_2Ph$ (0.11 mmol) in 1.1 mL $CH_2Cl_2$ was added. The reaction was stirred for 21 hours at low temperature and was quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by HPLC. The results of a number of experiments following this procedure using various ligands are reported in Table VII below.

TABLE VII

Effect of α,β-Unsaturated amide Substrate on Conjugate Addition

| Entry | α,β-Unsaturated amide | Time, h | %, yield | %, ee (stereochemistry) |
|---|---|---|---|---|
| 1 | (oxazolidinone-acryloyl-CH$_3$ structure) | 21 | 81 | 28 (R) |

TABLE VII-continued

Effect of α,β-Unsaturated amide Substrate on Conjugate Addition

| Entry | α,β-Unsaturated amide | Time, h | %, yield | %, ee (stereo-chemistry) |
|---|---|---|---|---|
| 2[a] | (pyrrolidinone crotonate structure) | 21 | 89 | 40 |
| 3 | (benzotriazole crotonate structure) | 21 | 15[b] | 21 (S) |

[a]Reaction performed at 0° C.
[b]Isolated as the methyl ester after methanolysis.

Example IX
Effect of Amine on Conjugate Addition

Under $N_2$, to a flask containing $MgBr_2 \cdot Et_2O$ (0.1 mmol) and bisoxazoline 2 (0.1 mmol) was added $CH_2Cl_2$ (3 mL). Pyrazole crotonate 1 (0.1 mmol) (in 1 mL $CH_2Cl_2$) was added and the mixture was allowed to stir for 30 min. The reaction was cooled to −60° C. and one of a variety of amines (0.11 mmol) in 1.1 mL $CH_2Cl_2$ was added. The reaction continued for 21 hours and then quenched with $H_2O$ and extracted 3 times with $CH_2Cl_2$. The combined organics were dried ($MgSO_4$) and concentrated to give an oil. The product was purified by preparative TLC or silica gel chromatography. The enantiomeric purity was determined by chiral HPLC. The results of a number of experiments following this procedure using various ligands are reported in Table VIII below.

TABLE VIII

Effect of Amine on Conjugate Addition

| Entry | Amine | %, Yield |
|---|---|---|
| 1 | $NH_2CH_2C_6H_5$ | ~80 |
| 2 | (3,5-dimethylpyrazole-NH structure) | ~87 |
| 3 | (diphenylmethylamine $NH_2$ structure) | ~50 |

Example X
Conjugate Addition of Morpholine to α,β-Unsaturated Amide (5)

Under $N_2$, to a flask containing $MgBr_2 \cdot Et_2O$ (0.1 mmol) and bisoxazoline 2 (0.1 mmol) was added $CH_2Cl_2$ (3 mL). α,β-Unsaturated amide 5 (0.1 mmol) (in 1 mL $CH_2Cl_2$) was added and the mixture was allowed to stir for 30 min. The reaction was cooled to −60° C. and morpholine (0.11 mmol) in 1.1 mL $CH_2Cl_2$ was added. The reaction continued for 21 hours and then quenched with $H_2O$ and extracted 3 times with $CH_2Cl_2$. The combined organics were dried ($MgSO_4$) and concentrated to give an oil. The reaction was monitored by NMR and proceeded to about 90% conversion of starting materials to product. The product proved too unstable for purification or determination of enantiomeric purity.

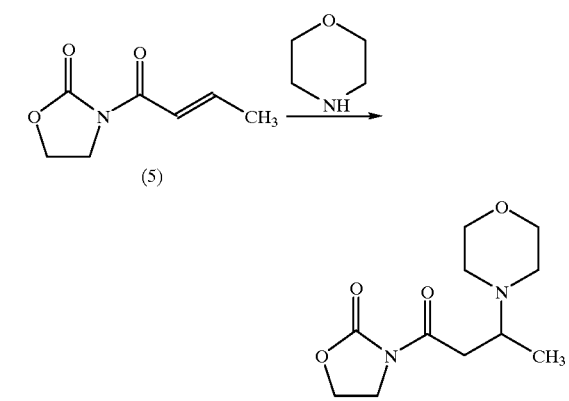

All publications and patent applications in this specification are indicative of the level of ordinary skill in the art to which this invention pertains. All publications and patent applications cited herein are hereby incorporated by reference to the same extent as if each individual publication or patent application was specifically and individually incorporated by reference.

The invention has been described with reference to various specific and preferred embodiments and techniques. However, it should be understood that many variations and modifications may be made while remaining within the spirit and scope of the invention.

What is claimed is:

1. A method for preparing a β-amino acid compound comprising:
   contacting an amine nucleophile with an α,β-unsaturated amide in the presence of a chiral Lewis acid complex to produce a chiral β-aminoamide;
   wherein the chiral Lewis acid complex is a chiral bisoxazolinylmethane compound with an azophilic metal cation salt.

2. The method of claim 1 wherein the azophilic metal cation includes $Zn^{2+}$, $Mg^{2+}$, $Sn^{2+}$, $Sc^{3+}$, $Y^{3+}$, a lanthanide cation or mixture thereof.

3. The method of claim 1 wherein the azophilic metal cation salt comprises a chlorine anion, bromine anion, iodine anion, triflate anion, or a mixture thereof.

4. The method of claim 1 wherein the chiral bisoxazolinylmethane compound has the formula:

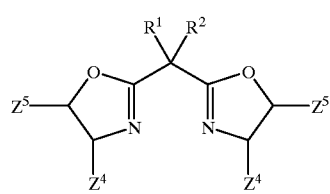

wherein $R^1$ and $R^2$ are independently hydrogen, alkyl, arylalkyl, or $R^1$ and $R^2$ together are —$(CH_2)_n$—, where n=2–6; and $Z^4$, $Z^{4'}$, $Z^5$, and $Z^{5'}$ are independently alkyl, cycloalkyl, aryl, or arylalkyl.

5. The method of claim 1 wherein the chiral bisoxazolinylmethane compound has the formula:

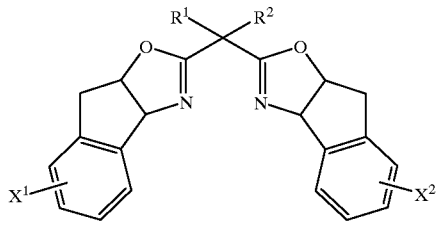

wherein $R^1$ and $R^2$ are independently hydrogen, alkyl, or arylalkyl, or $R^1$ and $R^2$ together are —$(CH_2)_n$—, where n=2–6;

$X^1$ and $X^2$ are independently hydrogen, alkyl, alkoxy, halo, haloalkyl, cyano, nitro, or $CO_2R'$; and wherein $R'$ is alkyl, cycloalkyl, or arylalkyl.

6. The method of claim 1 wherein the α,β-unsaturated amide has the formula:

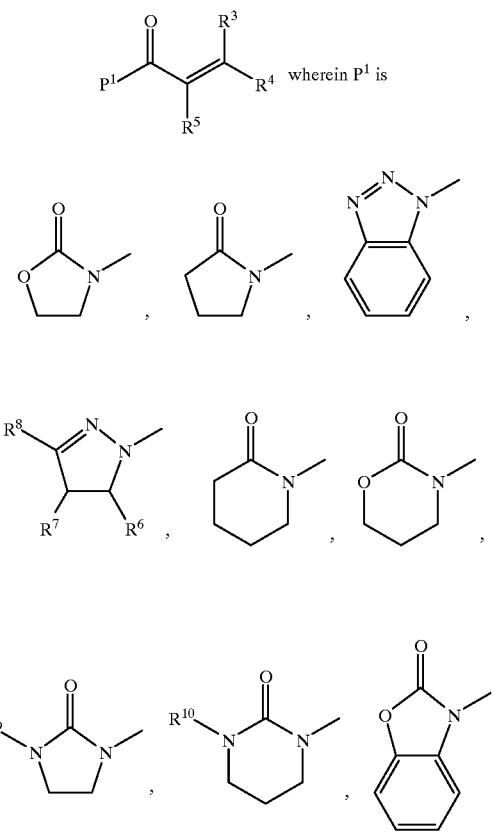

wherein $P^1$ is

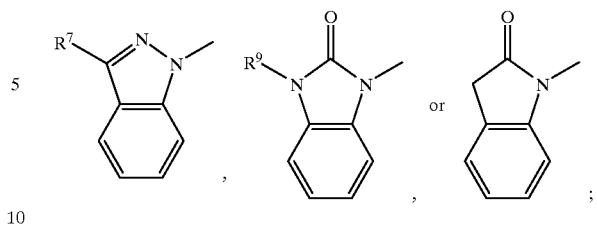

and $R^3$, $R^4$ and $R^5$ are independently hydrogen, alkyl, cycloalkyl, aryl, or arylalkyl, and at least one of $R^3$ and $R^4$ is not hydrogen, and $R^3$ and $R^4$ are not the same;

$R^6$ and $R^8$ are independently hydrogen, or $C_1$–$C_6$ alkyl;

$R^7$ is hydrogen, alkyl, arylalkyl, or aryl; and $R^9$ and $R^{10}$ are independently hydrogen, alkyl, cycloalkyl, aryl, or arylalkyl.

7. The method of claim 1 wherein the amine nucleophile includes a primary amine.

8. The method of claim 7 wherein the primary amine includes an hydroxylamine O-substituted with an alkyl, arylalkyl, or cycloalkyl group.

9. The method of claim 1 comprising contacting the amine nucleophile with an α,β-unsaturated amide compound in the presence of an organic solvent;

wherein the organic solvent includes acetonitrile, chlorinated organic solvent, ether solvent, aromatic solvent, or a mixture thereof.

10. The method of claim 1 wherein the molar ratio of the amine nucleophile to the α,β-unsaturated amide compound is from about 0.5:1 to about 1.2:1.

11. The method of claim 1 wherein the molar ratio of the azophilic metal cation salt to the α,β-unsaturated amide compound is from about 0.1:1 to about 1.0:1.

12. The method of claim 1 wherein the molar ratio of the chiral bisoxazolinylmethane compound to the azophilic metal cation salt is from about 1.0:1 to about 1.1:1.

13. The method of claim 1 wherein the chiral β-aminoamide includes a major enantiomer and a minor enantiomer; and further comprising reacting the minor enantiomer with the amine nucleophile in the presence of the chiral Lewis acid complex to produce an enantiomer of a second β-aminoamide having the formula:

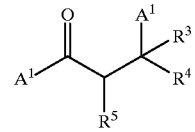

wherein $R^3$, $R^4$, and $R^5$ are independently hydrogen, alkyl, cycloalkyl, aryl, or arylalkyl, and at least one of $R^3$ and $R^4$ is not hydrogen; and $A^1$ is —$NHR^{16}$, —$N(OH)R^{16}$, —$N(OR^{16})H$, and $R^{16}$ is an alkyl, arylalkyl, or cycloalkyl group.

14. The method of claim 1 further comprising cleaving the chiral β-aminoamide to form a chiral β-$NH_2$-carboxamide or salt thereof.

15. The method of claim 14 comprising reductively cleaving the chiral β-aminoamide to form the chiral β-$NH_2$-carboxamide or salt thereof; wherein the amine nucleophile is an arylmethylamine, N-arylmethylhydroxylamine, O-arylmethylhydroxylamine, diarylmethylamine, O-diarylmethylhydroxylamine, or N-diarylmethylhydroxylamine.

16. The method of claim 1 further comprising hydrolyzing the chiral β-aminoamide to form a chiral β-aminocarboxylic acid or a salt thereof.

17. The method of claim 1 wherein the amine nucleophile is selected from the group consisting of $NH_2R^{16}$, $NH(OH)R^{16}$, and $N(OR^{16})H_2$, and $R^{16}$ is an alkyl, arylalkyl, or cycloalkyl group having no more than about 20 carbon atoms;

the azophilic metal cation salt is magnesium chloride or magnesium bromide;

the chiral bisoxazolinylmethane compound has the formula:

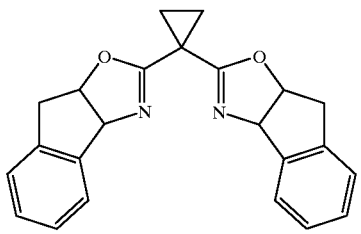

and the α,β-unsaturated amide has the formula:

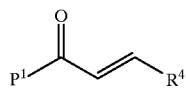

wherein $R^4$ is an alkyl, cycloalkyl, aryl, or arylalkyl group having no more than about 20 carbon atoms and $P^1$ is

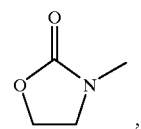,

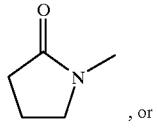, or

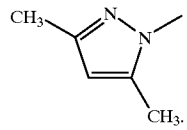

18. The method of claim 1 wherein the amine nucleophile is $NH_2R^{16}$ or $N(OR^{16})H_2$ and $R^{16}$ is an arylalkyl group.

19. The method of claim 18 wherein $R^{16}$ is benzyl or diphenylmethyl.

20. The method of claim 6 wherein $P^1$ is

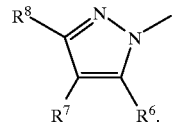

21. The method of claim 20 wherein $R^6$ and $R^8$ are methyl; $R^7$ is hydrogen.

* * * * *

UNITED STATES PATENT AND TRADEMARK OFFICE
CERTIFICATE OF CORRECTION

PATENT NO. : 6,080,857
DATED : June 27, 2000
INVENTOR(S) : Sibi et al.

It is certified that error appears in the above-identified patent and that said Letters Patent is hereby corrected as shown below:

Column 12,
Table IV: Replace the first ligand

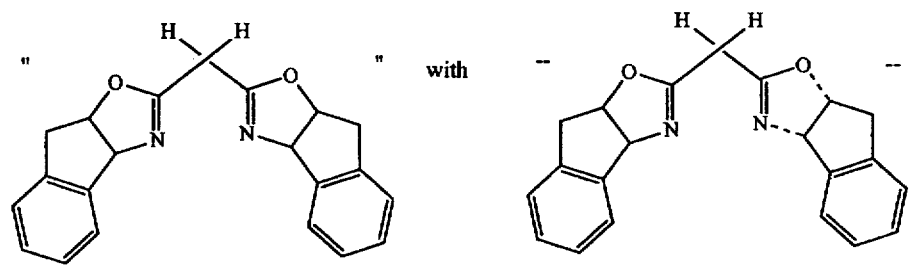

Replace the second ligand

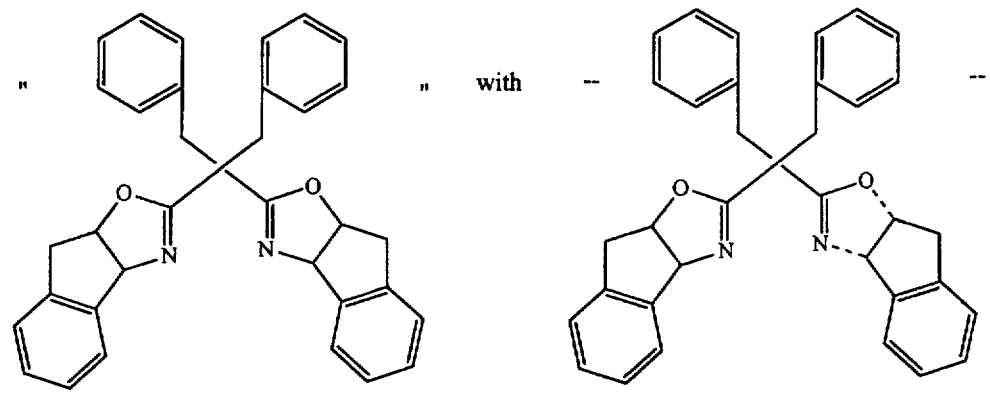

UNITED STATES PATENT AND TRADEMARK OFFICE
CERTIFICATE OF CORRECTION

PATENT NO. : 6,080,857
DATED : June 27, 2000
INVENTOR(S) : Sibi et al.

Page 2 of 2

It is certified that error appears in the above-identified patent and that said Letters Patent is hereby corrected as shown below:

Replace the third ligand

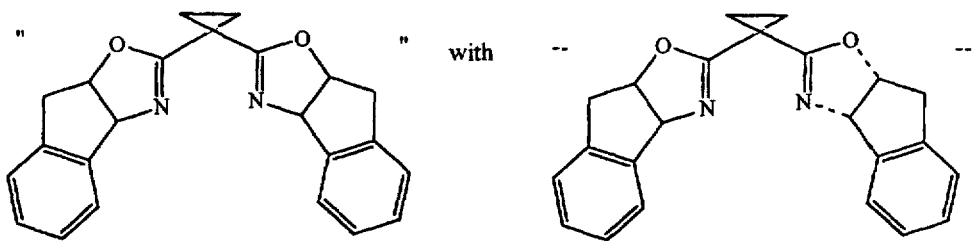

Signed and Sealed this

Twenty-ninth Day of January, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,080,857
DATED : June 27, 2000
INVENTOR(S) : Sibi et al.

It is certified that error appears in the above-identified patent and that said Letters Patent is hereby corrected as shown below:

<u>Title page,</u>
Add the following, Item [73], Assignee: "North Dakota State University" should read -- NDSU-Research Foundation --

Signed and Sealed this

Twenty-third Day of April, 2002

Attest:

*Attesting Officer*

JAMES E. ROGAN
*Director of the United States Patent and Trademark Office*